US012778866B2

(12) United States Patent
Fukui et al.

(10) Patent No.: US 12,778,866 B2
(45) Date of Patent: Nov. 3, 2026

(54) BETTER-FEELING ALCOHOL-BASED RUB-IN HAND SANITIZER COMPOSITION

(71) Applicant: SARAYA CO., LTD., Osaka (JP)

(72) Inventors: Takayuki Fukui, Kashiwara (JP); Takashi Takami, Kashiwara (JP); Yuichi Kumashita, Kashiwara (JP); Reiko Matsumura, Kashiwara (JP)

(73) Assignee: SARAYA CO., LTD., Osaka (JP)

( * ) Notice: Subject to any disclaimer, the term of this patent is extended or adjusted under 35 U.S.C. 154(b) by 292 days.

(21) Appl. No.: 18/574,582

(22) PCT Filed: Jan. 14, 2022

(86) PCT No.: PCT/JP2022/001044
§ 371 (c)(1),
(2) Date: Dec. 27, 2023

(87) PCT Pub. No.: WO2023/276203
PCT Pub. Date: Jan. 5, 2023

(65) Prior Publication Data

US 2024/0315936 A1 Sep. 26, 2024

(30) Foreign Application Priority Data

Jun. 30, 2021 (JP) ................................ 2021-109697

(51) Int. Cl.

| | |
|---|---|
| ***A61K 8/34*** | (2006.01) |
| ***A61K 8/37*** | (2006.01) |
| ***A61Q 17/00*** | (2006.01) |

(52) U.S. Cl.
CPC ................ *A61K 8/345* (2013.01); *A61K 8/37* (2013.01); *A61Q 17/005* (2013.01); *A61K 2800/70* (2013.01)

(58) Field of Classification Search
CPC .................................. A61K 8/34; A61K 8/37
See application file for complete search history.

(56) References Cited

U.S. PATENT DOCUMENTS

| | | | | |
|---|---|---|---|---|
| 6,136,771 A * | 10/2000 | Taylor | ...................... | C11D 1/83 510/342 |
| 2017/0181429 A1* | 6/2017 | Luciow | .................. | A01N 25/04 |

FOREIGN PATENT DOCUMENTS

| | | | |
|---|---|---|---|
| JP | H04-305504 A | | 10/1992 |
| JP | H06192065 | * | 7/1994 |
| JP | 2004-155712 A | | 6/2004 |
| JP | 2011-168524 A | | 9/2011 |
| JP | 2014-005209 A | | 1/2014 |
| JP | 5565902 | * | 8/2014 |
| JP | 2016-505576 A | | 2/2016 |
| KR | 10-2020-0034722 A | | 3/2020 |
| WO | WO 2014/100851 A1 | | 7/2014 |
| WO | 2019/006217 A1 | | 1/2019 |

OTHER PUBLICATIONS

Matsumura, "Efficacy of Virucidal Alcohol-Based Hand Antiseptics," *J. Antibact. Antifung. Agents*, 41(8): 421-425 (2013).
Pharmaceuticals and Medical Devices Agency, Medical Product Interview Form: "Quick-drying rub-in type hand sanitizer RABISHOT®" (2016).
Pharmaceuticals and Medical Devices Agency, Medical Product Interview Form: "Quick-drying rub-in type hand sanitizer RABIGEL®" (2016).
Japan Patent Office, International Starch Report in International Patent Application No. PCT/JP2022/001044 (Mar. 15, 2022).
Korea Ministry of Intellectual Property, Office Action in Korean Patent Application No. 10-2024-7003602 (Jul. 9, 2026).

* cited by examiner

*Primary Examiner* — Shirley V Gembeh
(74) *Attorney, Agent, or Firm* — Leydig, Voit & Mayer, Ltd.

(57) ABSTRACT

The present invention provides an alcohol-based rub-in hand sanitizer composition with a good feel in use. The alcohol-based rub-in hand sanitizer composition of the present invention is a liquid or viscous composition having a pH of 5.5 to 7.5 and comprising the following components: (A) a lower alcohol: 50 to 90 vol %; (B) at least one polyhydric alcohol selected from the group consisting of glycerin, 1,3-butylene glycol, and propylene glycol: 0.01 to 1.0 mass %; (C) isopropyl myristate and a glycerin fatty acid ester: each 0.01 to 0.12 mass %; and (D) water.

20 Claims, No Drawings

BETTER-FEELING ALCOHOL-BASED RUB-IN HAND SANITIZER COMPOSITION

TECHNICAL FIELD

The present invention relates to an alcohol-based rub-in hand sanitizer composition based on a lower alcohol, such as ethanol.

BACKGROUND ART

With the spread of the novel coronavirus infection (COVID-19) worldwide, there is growing recognition that hand hygiene is important as an infection control measure. Under these circumstances, the Ministry of Health, Labour and Welfare of Japan issued a notification stating that high-concentration alcohols (ethanol concentration: 70 to 83 vol %) are effective. For this reason, the demand for alcohol-based sanitizers based on lower alcohols is increasing not only for hand washing but also for disinfection in daily life.

On the other hand, as alcohol-based hand sanitizers have been used more frequently, many problems with alcohol-based hand sanitizers have been pointed out. First, the general problem with alcohol-based hand sanitizers is that as the alcohol evaporates, moisture in the skin decreases, causing the skin to lose its moisture, resulting in "rough hands." In addition, with liquid hand sanitizers (liquid type), problems such as "liquid overflowing from hands" and "liquid scattering" when spraying have been pointed out. On the other hand, viscous hand sanitizers (gel type) solve these problems of the liquid type; however, there is a new problem of poor feel in use, such as "slippery feeling."

Alcohol-based hand sanitizers are extremely useful not only against the novel coronavirus, but also against seasonal influenza and food poisoning. For this reason, in order to widely establish hand alcohol disinfection as a daily habit even in the post-coronavirus situation, in which the novel coronavirus infection has subsided, it is necessary to solve the above problems and develop alcohol-based hand sanitizers that can be used comfortably every day.

Various compositions for hand sterilization based on lower alcohols, such as ethanol, have been proposed.

For example, as a viscous microbicide composition that has a viscosity suitable for use, exhibits highly durable microbicidal activity after application, leaves the skin on the hands smooth (smooth feel), and has a high practical value, PTL 1 discloses a viscous microbicide composition having a pH of 5 to 8 and comprising 50 to 95 vol % of ethanol, 0.1 to 3.0 wt % of a carboxyvinyl polymer, 0.01 to 2.0 wt % of an alkanolamine, and 5 to 50 vol % of water, wherein a quaternary ammonium salt or a fatty acid ester can be added thereto. However, PTL 1 neither indicates nor suggests the combined use of a glycerin fatty acid ester and isopropyl myristate in a specific ratio as fatty acid esters.

In addition, as an inexpensive sterilizer/disinfectant for external use that has bactericidal activity effective against a wide range of microorganisms and safety (low toxicity), and that prevents rough hands even when used for hand disinfection, PTL 2 discloses a sterilizer/disinfectant for external use comprising 80 to 85 vol % of ethanol, 3.7 to 10 vol % of isopropanol, and one or more moisturizing components of glycerin, propylene glycol, sorbitol, 1,3-butylene glycol, polyethylene glycol, hyaluronate, and urea. However, PTL 2 neither indicates nor suggests the addition of fatty acid esters or the combined use of a glycerin fatty acid ester and isopropyl myristate in a specific ratio as fatty acid esters.

Furthermore, PTL 3 discloses an antiseptic hand rub composition comprising ethanol as a lower alcohol, wherein at least 0.2 w/w % of isopropyl myristate is added as an antipilling agent to improve the feel on the skin, and glycol and/or phenoxyethanol can be added. PTL 3 teaches that in a gel-like antiseptic hand rub composition comprising 70 v/v % ethanol, 0.3 w/w % Carbopol, 0.5 w/w % dipropylene glycol, and 0.2 w/w % isopropyl myristate, when the amount of isopropyl myristate was reduced to 0.1 w/w %, the smoothness disappeared and the dry feeling was enhanced compared to when no isopropyl myristate was added (see Table 8). PTL 3 also teaches that when glyceryl laurate, which is an emollient, was added in place of isopropyl myristate, the skin felt heavy and greasy (Table 4).

In addition, quick-drying rubbing-type hand sanitizers are on the market, which are effective against a wide range of microorganisms, including non-enveloped viruses, by containing 76.9 to 81.4 v/v % ethanol as an effective component and phosphoric acid as an additive to make them weakly acidic (pH: 3.0 to 4.0) (NPL 1 and NPL 2). It has been known that adjusting the pH of an alcohol solution to an acidic or alkaline range increases the inactivation effect on non-enveloped viruses, while bringing the pH closer to neutrality reduces the inactivation effect (NPL 3). For this reason, these quick-drying rubbing-type hand sanitizers take advantage of these characteristics of alcohol solutions. These rubbing-type hand sanitizers are divided into two types: liquid-type sanitizers containing, as additives, glycerin, allantoin, isopropyl myristate, glycerin fatty acid ester, ethyl paraoxybenzoate, N-coconut oil fatty acyl-L-arginine ethyl, and DL-pyrrolidone carboxylate, in addition to the phosphoric acid mentioned above (NPL 1); and gel-type sanitizers further containing hydroxypropyl cellulose (NPL 2).

CITATION LIST

Patent Literature

PTL 1: JPH04-305504A
PTL 2: JP2004-155712A
PTL 3: JP2016-505576A

Non-Patent Literature

NPL 1: Drug interview form "Quick-drying rubbing-type hand sanitizer Rabishot (registered trademark)" revised June 2016 (third edition)
NPL 2: Drug interview form "Quick-drying rubbing-type hand sanitizer Rabigel (registered trademark)" revised June 2016 (third edition)
NPL 3: Matsumura et al., "Efficacy of Virucidal Alcohol-Based Hand Antiseptics," Journal of Antibacterial and Antifungal Agents, Vol. 41, No. 8, pp. 421-425 (2013)

SUMMARY OF INVENTION

Technical Problem

An object of the present invention is to provide alcohol-based rub-in hand sanitizer compositions based on lower alcohols, such as ethanol. Preferably, an object of the present invention is to provide alcohol-based rub-in hand sanitizer compositions that are effective in preventing infections caused by various microorganisms, including the novel coronavirus, and that have an excellent feel in use for hands and fingers.

Solution to Problem

In the course of their daily research and development work, the present inventors have found that when polyhydric alcohols, such as glycerin, which are known as moisturizers, are added to liquid sanitizer compositions containing lower alcohols at a ratio of 50 to 90 v/v %, which is effective in preventing infections caused by various microorganisms, the moisture of the hands and fingers after rubbing is slightly improved, whereas there are problems in that there is a feeling of resistance when rubbing against the hands and fingers, there is a creaky or squeaky feeling after rubbing, and these tendencies increase as the amount of lower alcohol added increases. In order to solve these problems, the inventors conducted further study and confirmed that the feeling of resistance during rubbing and the squeaky feeling after rubbing were reduced, and the moisture was further increased by adding a combination of a specific amount of isopropyl myristate and a specific amount of glycerin fatty acid ester as fatty acid esters in addition to a specific amount of polyhydric alcohol.

In addition, in order to solve the problems of liquid sanitizer compositions, such as overflowing from hands or splashing around, the present inventors confirmed that when an acrylic acid polymer having thixotropic properties, such as a carboxyl vinyl polymer, as a thickener was added to liquid sanitizer compositions with a lower alcohol concentration of 50 to 90 v/v %, the resulting liquid sanitizer compositions were viscous when dispensed, thus solving the above problems, and became liquid when rubbed into the hands. On the other hand, it was found that when a polyhydric alcohol, such as glycerin, was added as a moisturizer to these compositions, the moisture of the hands and fingers after rubbing was slightly improved, whereas there was a feeling of resistance during rubbing and a squeaky feeling after rubbing, as with the liquid sanitizer compositions described above. As a means of solving these problems, it was confirmed that the method described above, that is, the method of adding a specific amount of isopropyl myristate and a specific amount of glycerin fatty acid ester as fatty acid esters in addition to a specific amount of polyhydric alcohol, was effective, and that combining both esters significantly suppressed the slippery and sticky feeling that occurred when only one of them was used, resulting in a moist and moisturizing feeling.

The present invention has been completed upon further study based on these findings, and includes the following embodiments.

(I) Liquid Rub-In Hand Sanitizer Composition (I-1) A rub-in hand sanitizer composition having a pH of 5.5 to 7.5 and comprising the following components:

(A) a lower alcohol: 50 to 90 vol %;

(B) at least one polyhydric alcohol selected from the group consisting of glycerin, 1,3-butylene glycol, and propylene glycol: 0.01 to 1.0 mass %;

(C) isopropyl myristate and a glycerin fatty acid ester: each 0.01 to 0.12 mass %; and (D) water.

(I-2) The rub-in hand sanitizer composition according to (I-1), wherein the lower alcohol is at least one member selected from ethanol, n-propyl alcohol, and isopropyl alcohol, and preferably ethanol.

(I-3) The rub-in hand sanitizer composition according to (I-1) or (I-2), wherein the ratio of isopropyl myristate and glycerin fatty acid ester as component (C) is such that the amount of glycerin fatty acid ester is 8 to 1200 parts by mass based on 100 parts by mass of isopropyl myristate.

(I-4) The rub-in hand sanitizer composition according to any one of (I-1) to (I-3), wherein the glycerin fatty acid ester as component (C) is one in which a $C_{6-16}$ saturated or unsaturated fatty acid is ester-bonded to one hydroxy group of glycerin.

(I-5) The rub-in hand sanitizer composition according to any one of (I-1) to (I-4), wherein the glycerin fatty acid ester as component (C) is a glycerin fatty acid ester other than lauric acid fatty acid esters, and preferably capric acid fatty acid ester.

(I-6) The rub-in hand sanitizer composition according to any one of (I-1) to (I-5), which is a liquid hand sanitizer composition.

(II) Viscous Rub-In Hand Sanitizer Composition (II-1) A rub-in hand sanitizer composition having a pH of 5.5 to 7.5 and comprising the following components:

(A) a lower alcohol: 50 to 90 vol %;

(B) at least one polyhydric alcohol selected from the group consisting of glycerin, 1,3-butylene glycol, and propylene glycol: 0.01 to 1.0 mass %;

(C) isopropyl myristate and a glycerin fatty acid ester: each 0.01 to 0.12 mass %;

(E) at least one acrylic acid polymer selected from the group consisting of carboxyvinyl polymers and acrylic acid-alkyl methacrylate copolymers;

(F) a pH adjuster; and (D) water.

(II-2) The rub-in hand sanitizer composition according to (II-1), wherein the lower alcohol is at least one member selected from ethanol, n-propyl alcohol, and isopropyl alcohol, and preferably ethanol.

(II-3) The rub-in hand sanitizer composition according to (II-1) or (II-2), wherein the ratio of isopropyl myristate and glycerin fatty acid ester as component (C) is such that the amount of glycerin fatty acid ester is 8 to 1200 parts by mass, and preferably 10 to 100 parts by mass, based on 100 parts by mass of isopropyl myristate.

(II-4) The rub-in hand sanitizer composition according to any one of (II-1) to (II-3), wherein the glycerin fatty acid ester as component (C) is one in which a $C_{6-16}$ saturated or unsaturated fatty acid is ester-bonded to one hydroxy group of glycerin.

(II-5) The rub-in hand sanitizer composition according to any one of (II-1) to (II-4), wherein the glycerin fatty acid ester as component (C) is a glycerin fatty acid ester other than lauric acid fatty acid esters, and preferably capric acid fatty acid ester.

(II-6) The rub-in hand sanitizer composition according to any one of (II-1) to (II-5), wherein the carboxyvinyl polymer as component (E) has the following characteristics:

the viscosity of a 0.2 w/v % aqueous solution (pH: 7.0-7.5, 20±1° C.) measured with a Brookfield rotational viscometer (No. 2 or No. 4, 12 rotations) is 1500 to 50000 mPa·s, preferably 1500 to 30000 mPa·s, and more preferably 1500 to 7500 mPa·s.

(II-7) The rub-in hand sanitizer composition according to any one of (II-1) to (II-6), wherein the acrylic acid-alkyl methacrylate copolymer as component (F) is an (acrylates/alkyl acrylate (C10-30)) crosspolymer having the following characteristics:

the viscosity of a 0.5 w/v % aqueous solution (pH: 7.0-7.5, 20±1° C.) measured with a Brookfield rotational viscometer (No. 2 or No. 4, 12 rotations) is 25000 to 65000 mPa·s, and preferably 45000 to 65000 mPa·s.

(II-8) The rub-in hand sanitizer composition according to any one of (II-1) to (II-7), wherein the pH adjuster as component (F) is at least one water-soluble or alcohol-soluble amine compound selected from the group consisting of triethanolamine, aminomethylpropanol, tromethamine, tetrahydroxypropyl ethylenediamine, diisopropanolamine, and PEG-15 Cocamine.

(II-9) The rub-in hand sanitizer composition according to any one of (II-1) to (II-8), which is a viscous hand sanitizer composition.

Advantageous Effects of Invention

The hand sanitizer compositions of the present invention are characterized by being gentle on the hands and fingers, and having an excellent feel in use, despite their high alcohol content. Specifically, the liquid hand sanitizer composition has less resistance when rubbed into the hands and fingers, and is easy to rub in, and after rubbing in, it has a less squeaky feeling and can impart a moisturizing feeling to the hands and fingers. The viscous hand sanitizer composition allows the gel-like liquid to be distributed over the entire object to be disinfected, such as hands and fingers, without the problem of overflowing or dripping from the hands and fingers, as with the liquid hand sanitizer composition. Although it has some viscosity when dispensed, it becomes liquid-like when rubbed into the hands and fingers, and is easy to rub in with little resistance. Furthermore, after rubbing in, it has a less squeaky or slippery feeling and can impart a moisturizing feeling to the hands and fingers. Thus, the present invention can prepare and provide hand sanitizer compositions that have an excellent feel in use and can effectively disinfect, for example, the skin of hands and fingers.

DESCRIPTION OF EMBODIMENTS

The rub-in hand sanitizer compositions of the present invention include a liquid hand sanitizer composition (liquid type) and a viscous hand sanitizer composition (gel type).

(I) Liquid Rub-In Hand Sanitizer Composition

The liquid hand sanitizer composition is characterized by having a pH within the range of 5.5 to 7.5 and comprising the following (A) to (D):

(A) a lower alcohol present in an amount of 50 to 90 vol % based on the entire composition;

(B) at least one polyhydric alcohol selected from the group consisting of glycerin, 1,3-butylene glycol, and propylene glycol, present in an amount of 0.01 to 1.0 mass % based on the entire composition;

(C) isopropyl myristate and a glycerin fatty acid ester each present in an amount of 0.01 to 0.12 mass % based on the entire composition; and (D) water present in an amount that makes the entire composition 100 mass %.

Each of these components is explained below.

(A) Lower Alcohol

The lower alcohol used in the present invention is a lower hydrocarbon chain alcohol with bactericidal action. Specific examples include ethanol, n-propyl alcohol, and isopropyl alcohol. Preferred is ethanol. These lower alcohols may be used singly or in combination of two or more.

The hand sanitizer composition of the present invention (100 vol %) may contain such a lower alcohol in an amount ranging from 50 to 90 vol %. The lower limit is not particularly limited as long as it is 50 vol % or more, but may be preferably 60 vol % or more, and more preferably 70 vol % or more, in terms of bactericidal activity. Further, the upper limit is not particularly limited as long as it is 90 vol % or less, but may be preferably 85 vol % or less, and more preferably 80 vol % or less. Although it is not limited, when ethanol is singly used as the lower alcohol, the specific range is, for example, 50 to 90 vol %, preferably 70 to 85 vol %, and particularly preferably 75 to 82 vol %. Further, when n-propyl alcohol or isopropyl alcohol is singly used as the lower alcohol, the specific range is, for example, 50 to 90 vol %, preferably 70 to 85 vol %, and particularly preferably 75 to 82 vol %.

(B) Polyhydric Alcohol

The polyhydric alcohol used in the present invention is at least one member selected from the group consisting of glycerin, 1,3-butylene glycol, and propylene glycol. These polyhydric alcohols may be used singly or in combination of two or more. Preferred is glycerin.

The hand sanitizer composition of the present invention (100 mass %) may contain such a polyhydric alcohol in a total amount ranging from 0.01 to 1.0 mass %. When a polyhydric alcohol is contained in this range, it is possible to obtain a hand sanitizer composition that is easy to rub in with little resistance when rubbed into the hands and fingers, does not have a squeaky or slippery feeling after rubbing, and can impart a moisturizing feeling to the hands and fingers. The lower limit is not particularly limited as long as it is 0.01 mass % or more, but may be preferably 0.05 mass % or more, and more preferably 0.1 mass % or more. Further, the upper limit is not particularly limited as long as it is 1.0 mass % or less, but may be preferably 0.8 mass % or less, and more preferably 0.5 mass % or less. The specific range is, for example, preferably 0.05 to 0.8 mass %, and more preferably 0.1 to 0.5 mass %.

(C) Isopropyl Myristate and Glycerin Fatty Acid Ester

The hand sanitizer composition of the present invention is characterized by comprising isopropyl myristate and a glycerin fatty acid ester in a specific ratio.

Isopropyl myristate is a fatty acid ester in which the carboxy group of myristic acid and the hydroxyl group of isopropyl alcohol are ester-bonded. The hand sanitizer composition of the present invention (100 mass %) may contain isopropyl myristate in an amount ranging from 0.01 to 0.12 mass %. When isopropyl myristate is contained in this range in addition to lower alcohol (A) and polyhydric alcohol (B) described above, and glycerin fatty acid ester (C) described later, it is possible to obtain a hand sanitizer composition that is easy to rub in with little resistance when rubbed into the hands and fingers, does not have a squeaky or slippery feeling after rubbing, and can impart a moisturizing feeling to the hands and fingers. The lower limit is not particularly limited as long as it is 0.01 mass % or more, but may be preferably 0.02 mass % or more, and more preferably 0.03 mass % or more. Further, the upper limit is not particularly limited as long as it is 0.12 mass % or less, but may be preferably 0.10 mass % or less, and more preferably 0.08 mass % or less. The specific range is, for example, preferably 0.02 to 0.1 mass %, and more preferably 0.03 to 0.08 mass %.

The glycerin fatty acid ester is monoacylglycerol or diacylglycerol with a fatty acid ester-bonded to one or two of the three hydroxyl groups of glycerin. Monoacylglycerol is suitably used in the present invention. Examples of the fatty acid bonded to the hydroxyl group(s) of glycerin include $C_{6-16}$ saturated fatty acids. Preferred are $C_{8-14}$, and more preferably $C_{8-12}$, saturated fatty acids, and particularly preferred are $C_{10}$ saturated fatty acids.

The hand sanitizer composition of the present invention (100 mass %) may contain a glycerin fatty acid ester in an amount ranging from 0.01 to 0.12 mass %. When a glycerin fatty acid ester is contained in this range in addition to lower alcohol (A), polyhydric alcohol (B), and isopropyl myristate (C) described above, it is possible to obtain a hand sanitizer composition that is easy to rub in with little resistance when rubbed into the hands and fingers, does not have a squeaky or slippery feeling after rubbing, and can impart a moisturizing feeling to the hands and fingers. The lower limit is not particularly limited as long as it is 0.01 mass % or more. Further, the upper limit is not particularly limited as long as it is 0.12 mass % or less, but may be preferably 0.10 mass % or less, and more preferably 0.06 mass % or less. The specific range is, for example, preferably 0.01 to 0.1 mass %, and more preferably 0.01 to 0.06 mass %.

The ratio of isopropyl myristate and a glycerin fatty acid ester as component (C) is not limited, but is preferably such that the amount of glycerin fatty acid ester can be selected from 8 to 1200 parts by mass, and preferably 10 to 100 parts by mass, based on 100 parts by mass of isopropyl myristate.

(D) Water

The hand sanitizer composition of the present invention is an aqueous composition containing water as a solvent.

The hand sanitizer composition of the present invention has antimicrobial action (antiviral effect, antibacterial effect) and is used for disinfection of hands and figures. Therefore, the water used as its solvent is required not to impair these effects (antimicrobial properties). Specifically, purified water can be used. Purified water mentioned here refers to water that has been purified by applying necessary water treatment operations to raw water (river water and groundwater that serve as raw materials). Preferred examples of tap water include water that meets or exceeds the water quality standards stipulated in the Water Supply Service Act and the Ministerial Ordinance on Water Quality Standards. Specific examples include tap water, sterile water, RO water, ion exchange water, distilled water, purified water, alkaline ionized water, deep ocean water, and the like. Preferred is purified water.

Water can be mixed in an amount that makes the total amount of the hand sanitizer composition of the present invention 100 mass %.

(E) pH of Hand Sanitizer Composition and pH Adjuster

The hand sanitizer composition of the present invention is characterized by being adjusted to a pH of 5.5 to 7.5. The range of pH is preferably 6.0 to 7.2, and more preferably 6.2 to 7.0, because of feel in use and being gentle on the skin of the hands and fingers.

In order to adjust the pH of the hand sanitizer composition of the present invention within the above range, a pH adjuster can be used as required. However, if the pH can be adjusted within the above range by mixing components (A) to (D) described above, it is not particularly necessary to add a pH adjuster. As the pH adjuster, an acid, a base, an amine and/or a salt thereof can be suitably selected and used depending on the pH of the hand sanitizer composition prepared by mixing components (A) to (D) etc. Specific examples of acids include inorganic acids, such as hydrochloric acid, sulfuric acid, and nitric acid; and organic acids, such as lactic acid, citric acid, malic acid, and phosphoric acid. Specific examples of bases include inorganic bases, such as sodium hydroxide, potassium hydroxide, and ammonium hydroxide. Specific examples of amines include triethanolamine, aminomethylpropanol, tromethamine, tetrahydroxypropyl ethylenediamine, diisopropanolamine, and PEG-15 Cocamine. In terms of high affinity for relatively high-concentration alcohol-containing aqueous solutions, triethanolamine, tetrahydroxypropyl ethylenediamine, diisopropanolamine, di(2-ethylhexyl)amine, and PEG-15 Cocamine are suitably used as amines.

(G) Other Components

The hand sanitizer composition of the present invention may contain other components as long as, in addition to the antimicrobial action, the effects of the present invention and the liquid state are not impaired. Examples of such other components include fragrances, pigments (colorants), antioxidants, blood circulation promoters, and the like.

In the hand sanitizer composition of the present invention, the high-concentration lower alcohol component contained therein acts as a disinfectant substance (antiviral substance, antibacterial substance) as described above, and it is thus not necessary to separately add an antibacterial agent. However, this does not limit the mixing of antibacterial agents as long as the effects of the present invention are not impaired. However, it is preferable not to mix antibacterial agents that are highly irritating to the skin or that can cause rough hands, such as povidone-iodine and triclosan. Examples of antibacterial agents that can be mixed include biguanide-based antibacterial agents, such as chlorhexidine gluconate and olanexidine gluconate; quaternary ammonium salts, such as benzalkonium chloride and benzethonium chloride; glycine-based amphoteric surfactants, such as dialkylaminoethylglycine; natural antibacterial agents, such as essential oils, plant extracts, polyphenols, catechins, chitin, chitosan, hinokitiol, lysozyme, amino acids, and dipeptides; and the like.

In addition, since the hand sanitizer composition of the present invention contains components (A) to (D) described above, it is possible to obtain a hand sanitizer composition that is easy to rub in with little resistance when rubbed into the hands and fingers, does not have a squeaky or slippery feeling after rubbing, and can impart a moisturizing feeling to the hands and fingers. Therefore, it is not necessary to separately mix other components called emollients or moisturizers. Rather, it is preferable not to mix such components because the balance between components (A) to (D) is disrupted. The term "emollients" here broadly refers to materials that can maintain or improve the moisture level, compliance, or appearance of the skin when used repeatedly on the skin, such as on the hands and fingers. In this sense, this term includes moisturizers.

Examples of emollients include allantoin, amino acids (e.g., glycine and alanine), sugar alcohols (e.g., sorbitol, erythritol, xylitol, maltitol, lactitol, and mannitol), diisobutyl adipate, lanolin, vinyl alcohol, polyvinylpyrrolidone, polyols (e.g., glyceryl oleate and sorbitol), polyethylene glycol, coco-glucoside, fatty alcohols (e.g., cetyl alcohol, stearyl alcohol, lauryl alcohol, myristyl alcohol, alkoxylated cetyl alcohol, and palmityl alcohol), Ceteareth 20, dexpanthenol, squalene, glycerin triisooctanoate, coconut oil fatty acid PEG-7 glyceryl, ceramide, vegetable oils (e.g., jojoba seed oil, sugar squalane, and olive oil), sodium hyaluronate, sodium 2-pyrrolidone-5-carboxylate, urea, sodium lactate, 2-methacryloyloxyethyl phosphorylcholine/butyl methacrylate copolymer liquid, plant extracts such as chamomile extract, and the like.

It is preferable that the hand sanitizer composition of the present invention does not contain components that are highly irritating to the skin or that cause rough hands. Examples of such components include antiseptics, aldehyde-based sanitizers such as glutaraldehyde, chlorine-based sanitizers such as sodium hypochlorite, iodine-based sanitizers such as povidone-iodine, phenol-based sanitizers such as cresol, and the like.

The liquid hand sanitizer composition can be placed in a container with a hinged cap that can dispense the hand sanitizer composition as a liquid, or a spray container that can dispense the hand sanitizer composition as mist-like droplets, and then be used by spraying it onto the hands and fingers. Examples of the spray container include, without any limitation, portable spray containers and containers with hand spray pumps or dispensers. Preferred are non-gas dispensers. The liquid state means the state in which it can be placed in an ordinary spray container (non-gas container) and dispensed by spraying, and is not limited thereto as far as this goes. The dispenser for containing the liquid hand sanitizer composition is not limited. For example, in the case of a spray container, it may be capable of dispensing 1 to 3 mL of atomized liquid (volume converted to liquid amount) per push.

(II) Viscous Rub-In Hand Sanitizer Composition

The viscous hand sanitizer composition is characterized by having a pH within the range of 5.5 to 7.5 and comprising the following (A) to (F):

(A) a lower alcohol present in an amount of 50 to 90 vol % based on the entire composition;

(B) at least one polyhydric alcohol selected from the group consisting of glycerin, 1,3-butylene glycol, and propylene glycol, present in an amount of 0.01 to 1.0 mass % based on the entire composition;

(C) isopropyl myristate and a glycerin fatty acid ester each present in an amount of 0.01 to 0.12 mass % based on the entire composition;

(E) a pH adjuster;

(F) at least one acrylic acid polymer selected from the group consisting of carboxyvinyl polymers and acrylic acid-alkyl methacrylate copolymers; and (D) water present in an amount that makes the entire composition 100 mass %.

Among these components, (A) to (E), including the mixing ratio, are as described above regarding the liquid rub-in hand sanitizer composition, and the above descriptions can be incorporated herein by reference.

(F) Acrylic Acid Polymer

The acrylic acid polymer used in the present invention is at least one member selected from the group consisting of carboxyvinyl polymers and acrylic acid-alkyl methacrylate copolymers. These acrylic acid polymers may be used singly or in combination of two or more. Preferred is a carboxyvinyl polymer.

The carboxyvinyl polymer is a water-soluble acrylic acid polymer with acrylic acid as the main chain and crosslinked with allyl sucrose, pentaerythritol, etc. A suitably used carboxyvinyl polymer has a carboxyl group content of preferably 57.7 to 63.4%, and more preferably 58 to 63%.

The carboxyvinyl polymer should conform with Japanese Pharmaceutical Excipients 2018 (Ministry of Health, Labour and Welfare of Japan, Pharmaceutical Safety and Environmental Health Bureau, Pharmaceutical Evaluation Division) (hereinafter also referred to as "JPE2018"). Specifically, the following carboxyvinyl polymer can be used: a sample solution (20±0.1° C.) prepared by dispersing 0.4 g of dried carboxyvinyl polymer in 200 ml of water and then adjusting the pH to 7.0 to 7.5 using an aqueous sodium hydroxide solution is allowed to stand for 10 hours to remove air bubbles, and then the viscosity measured with a Brookfield rotational viscometer is 1500 mPa·s (No. 2, 12 rotations, 30 seconds) to 50000 mPa·s (No. 4, 12 rotations, stable). Preferred is a carboxyvinyl polymer with a viscosity of 1500 to 30000 mPa·s, and more preferably 1500 to 7,500 mPa·s.

The mixing ratio into the hand sanitizer composition of the present invention (100 mass %) can be suitably adjusted depending on the viscosity of the carboxyvinyl polymer used.

For example, when a carboxyvinyl polymer with a viscosity of 1500 to 10000 mPa·s is used, the range of the mixing ratio is, for example, 0.01 to 1.0 mass %, preferably 0.05 to 0.9 mass %, and more preferably 0.1 to 0.8 mass %; when a carboxyvinyl polymer with a viscosity of 10000 to 30000 mPa·s is used, the range of the mixing ratio is, for example, 0.01 to 1.0 mass %, preferably 0.05 to 0.8 mass %, and more preferably 0.1 to 0.7 mass %; and when a carboxyvinyl polymer with a viscosity of 30000 to 50000 mPa·s is used, the range of the mixing ratio is, for example, 0.01 to 1.0 mass %, preferably 0.05 to 0.7 mass %, and more preferably 0.1 to 0.6 mass %.

As a result of the neutralization of the carboxyvinyl polymer with salt (alkali), the carboxyl groups are negatively charged along the polymer backbone, which thickens the polymer by its repulsive force. Therefore, the carboxyvinyl polymer is used in combination with an inorganic base or an amine among pH adjusters (E) described above. An amine is preferably used as pH adjuster (E) used in combination with the carboxyvinyl polymer. More preferred are triethanolamine, aminomethylpropanol, tetrahydroxypropyl ethylenediamine, diisopropanolamine, and PEG-15 Cocamine, in terms of high affinity for the relatively high-concentration alcohol-containing aqueous solution. Particularly preferred is triethanolamine.

The acrylic acid-alkyl methacrylate copolymer is a copolymer in which a $C_{1030}$ alkyl methacrylate group is introduced into polyacrylic acid. This copolymer is also known as an (acrylates/alkyl acrylate (C10-30)) crosspolymer.

The acrylic acid-alkyl methacrylate copolymer should conform with the Japanese Standards of Quasi-drug Ingredients 2021 (Ministry of Health, Labour and Welfare of Japan, Pharmaceutical Safety and Environmental Health Bureau, Pharmaceutical Evaluation Division) (hereinafter also referred to as "JSQI 2021"). Examples include those in which the viscosity of a 0.5 w/v % aqueous solution (pH: 7.0-7.5, 20±1° C.) measured with a Brookfield rotational viscometer (No. 2 or No. 4, 12 rotations) is 25000 to 65000 mPa·s, and preferably 45000 to 65000 mPa·s.

The mixing ratio into the hand sanitizer composition of the present invention (100 mass %) can be suitably adjusted depending on the viscosity of the acrylic acid-alkyl methacrylate copolymer used.

For example, when an acrylic acid-alkyl methacrylate copolymer with a viscosity of 25000 to 45000 mPa·s is used, the range of the mixing ratio is, for example, 0.01 to 1.0 mass %, preferably 0.05 to 0.8 mass %, and more preferably 0.1 to 0.7 mass %; when an acrylic acid-alkyl methacrylate copolymer with a viscosity of 45000 to 65000 mPa·s is used, the range of the mixing ratio is, for example, 0.01 to 1.0 mass %, preferably 0.05 to 0.7 mass %, and more preferably 0.1 to 0.6 mass %.

As a result of the neutralization of the acrylic acid-alkyl methacrylate copolymer with salt (alkali), the carboxyl groups are negatively charged along the polymer backbone, which thickens the polymer by its repulsive force. Therefore, the acrylic acid-alkyl methacrylate copolymer is used in combination with an inorganic base or an amine among pH adjusters (E) described above, as with the carboxyvinyl polymer. An amine is preferably used as pH adjuster (E) used in combination with the carboxyvinyl polymer. More preferred are triethanolamine, aminomethylpropanol, tetrahydroxypropyl ethylenediamine, diisopropanolamine, and PEG-15 Cocamine, in terms of high affinity for the relatively high-concentration alcohol-containing aqueous solution. Particularly preferred is triethanolamine.

(G) Other Components

As with the liquid hand sanitizer composition described above, the viscous hand sanitizer composition may also contain other components as long as, in addition to the antimicrobial action, the effects of the present invention and the viscous (gel) state are not impaired. As with the liquid hand sanitizer composition, it is preferable not to mix components that impair the effects of the present invention, such as components that are highly irritating to the skin or that cause rough hands. In addition, since the viscous hand sanitizer composition of the present invention contains components (A) to (F) described above, it is possible to obtain a hand sanitizer composition that is easy to rub in with little resistance when rubbed into the hands and fingers, does not have a squeaky or slippery feeling after rubbing, and can impart a moisturizing feeling to the hands and fingers. Therefore, as with the liquid hand sanitizer composition described above, it is not necessary to separately mix other components called emollients or moisturizers. Rather, it is preferable not to mix such components because the balance between components (A) to (F) is disrupted.

The viscous hand sanitizer composition can be placed in a container that can dispense the hand sanitizer composition as a gel-like liquid, and then be used by dispensing it onto the hands and fingers. Examples of containers include, without any limitation, tube containers, push-out containers (including containers with hinged caps), and containers with hand pumps or dispensers, all of which can dispense gel. The dispenser for containing the viscous hand sanitizer composition is not limited, but may be capable of dispensing 1 to 2 mL of gel-like liquid (volume converted to liquid amount) per dispense.

As described above, the liquid and viscous hand sanitizer compositions of the present invention each have an alcohol content of, up to 90 vol %, 50 vol % or more, and preferably 60 vol % or more, based on the entire amount (100 vol %) of the composition. For this reason, without other additives with additional antibacterial effects (antibacterial agents) etc., these compositions exhibit antiviral activity against viruses covered with an envelope (enveloped virus), such as coronaviruses, influenza viruses, herpes viruses, and hepatitis C and B viruses. Therefore, the hand sanitizer compositions of the present invention can be suitably used for disinfecting the skin, including hands and fingers (antibacterial treatment, antiviral treatment).

Further, the hand sanitizer compositions of the present invention are characterized by being gentle on the hands and fingers, and having an excellent feel in use, despite their high alcohol content. Specifically, the liquid hand sanitizer composition has less resistance when rubbed into the hands and fingers, and is easy to rub in, and after rubbing in, it has a less squeaky feeling and can impart a moisturizing feeling to the hands and fingers. The viscous hand sanitizer composition allows the gel-like liquid to be distributed over the entire object to be disinfected, such as hands and fingers, without the problem of overflowing or dripping from the hands and fingers, as with the liquid hand sanitizer composition. Although it has some viscosity when dispensed, it becomes liquid-like when rubbed into the hands and fingers, and is easy to rub in with little resistance. Furthermore, after rubbing in, it has a less squeaky or slippery feeling and can impart a moisturizing feeling to the hands and fingers. Thus, the present invention can prepare and provide hand sanitizer compositions that have an excellent feel in use and can effectively disinfect, for example, the skin of hands and fingers.

Production Method

The liquid hand sanitizer composition of the present invention can be produced by mixing (A) to (D) described above and optionally other components, and adjusting the pH to a desired range of 5.5 to 7.5. Further, the viscous hand sanitizer composition of the present invention can be produced by mixing (A) to (F) described above and optionally other components, and adjusting the pH to a desired range of 5.5 to 7.5. The thus-prepared hand sanitizer compositions of the present invention can be stored in the dispensers described above according to their properties, and thus prepared as actual products to be actually used. They can also be stored in replacement containers.

(III) Use of Sanitizer Compositions of the Present Invention

The hand sanitizer compositions of the present invention can be used as skin sanitizers, particularly as hand sanitizers, based on their antimicrobial action described above. The term “sanitize” means to prevent the growth of harmful microorganisms to kill them or reduce the number of microorganisms. In this sense, the term “sanitize” is used to include antibacterial (antiviral) and sterilization (virus inactivation). The harmful microorganisms particularly targeted by the present invention include, as described above, enveloped viruses, such as coronaviruses, influenza viruses, herpes viruses, and hepatitis C and B viruses. Thus, the hand sanitizer compositions of the present invention can be effectively used to prevent infections caused by these viruses.

The terms “comprising” and “containing” in this specification include the meaning of consisting of and consisting essentially of.

EXAMPLES

The following describes the present invention with reference to experimental examples to facilitate understanding of the elements and effects of the invention. However, the invention is not limited in any way by these experimental examples. The following experiments were conducted at room temperature (25±5° C.) under atmospheric pressure, unless otherwise noted. Unless otherwise specified, the unit “%” below indicates mass %, and the unit “parts” indicates parts by mass.

The components used in the following Examples are as follows:

Ethanol: Japanese Pharmacopoeia ethanol 95 v/v %

Isopropyl alcohol: 99% or more n-Propyl alcohol: 99% or more

Glycerin: concentrated glycerin (glycerin concentration 98%)

1,3-Butylene glycol: 99% or more

Propylene glycol: 99% or more

Isopropyl myristate: NIKKOL IPM-EX (produced by Nikko Chemicals Co., Ltd.)

Glycerin fatty acid ester: Sunsoft No. 760-C (glyceryl caprate, medium-chain fatty acid monoglyceride: produced by Taiyo Kagaku Co., Ltd.)

Carboxyvinyl polymer: AQUPEC HV-801EG (manufacturer information: 0.2% aqueous solution viscosity: 2,500-6,400 mPa·s, 0.5% aqueous solution viscosity: 5,400-11,400 mPa·s, pH: 2.7 to 3.3) (produced by Sumitomo Seika Chemicals Co., Ltd.)

(Acrylates/alkyl acrylate (C10-30)) crosspolymer: Carbopol SC-500 Polymer (produced by Lubrizol)

Experimental Example 1: Preparation and Evaluation of Liquid Rub-in Hand Sanitizer Compositions The components shown in Tables 2 and 3 were mixed to prepare liquid rub-in hand sanitizer compositions (test samples 1-1 to 1-30, pH: 6.5 to 7). These compositions were each placed in a spray container with a single discharge amount set to 1 ml.

Ten panelists evaluated the feel in use when each of the test samples 1-1 to 1-30 was rubbed into the hands and fingers (during rubbing and after rubbing) in the following manner. The 10 panelists are all researchers with specialized training in sensory evaluation and have passed in-house sensory evaluation tests.

Test Method

1. Before each test sample was rubbed in, every time, both hands were washed thoroughly with 5% potassium soap and running water (tap water), and then wiped lightly with a dry paper towel.
2. The test sample placed in the spray container was then dispensed once (1 ml) on the hands, and both hands were rubbed until the liquid dried, thereby rubbing it all over the hands and fingers.
3. After rubbing in, each panelist evaluated the feel in use (during rubbing and after rubbing) according to the determination table shown in Table 1.
4. For each evaluation item, the average of the evaluation scores of each panelist was calculated and evaluated according to the following criteria.

A: an average of 2.0 points or more
B: an average of 1.0 to less than 2.0 points
C: an average of less than 1.0 point The 10 panelists discussed the criteria for each item in the determination table shown in Table 1 with each other in advance and confirmed that all panelists were in a condition to evaluate the items using the same criteria, after which this test was conducted as described above.

TABLE 1

Table 1 (determination table)

| Time of evaluation | Evaluation item | 0 points Poor | 1 point Slightly poor | 2 points Slightly good | 3 points Good |
|---|---|---|---|---|---|
| During rubbing | Resistance and ease of rubbing | Resistance felt just before drying, and difficult to rub in | Slight resistance felt just before dying, and a little more difficult to rub in | No resistance just before drying, and a little easier to rub in | Smooth feeling and easy to rub in |
| After rubbing | Squeakiness | Creaky and squeaky | Slightly creaky and a little squeaky | Hardly feels squeaky and feels slightly smooth | Feels smooth without being squeaky |
| | Moisture | Flaky and dry | Not flaky, but does not feel moisturized | Slight moist feeling, and feels moisturized | Moist feeling and feels moisturized |
| | Slipperiness | Slippery feeling, and slipperiness is a concern | Slight slipperiness | Slight slipperiness right after drying, but soon becomes unnoticeable | No slipperiness |

Tables 2 and 3 show the test results.

TABLE 2

Table 2 (liquid rub-in hand sanitizer composition)

mass %

| | Component | | Test sample 1-1 | 1-2 | 1-3 | 1-4 | 1-5 | 1-6 | 1-7 |
|---|---|---|---|---|---|---|---|---|---|
| A | Ethanol* | | 78.1 | 78.1 | 78.1 | 78.1 | 78.1 | 78.1 | 78.1 |
| | Isopropanol | | — | — | — | — | — | — | — |
| | n-Propyl alcohol | | — | — | — | — | — | — | — |
| B | Glycerin | | — | 0.01 | 0.5 | 1 | 1.5 | 2 | 0.5 |
| C | Isopropyl myristate | | — | — | — | — | — | — | 0.01 |
| | Glycerin fatty acid ester | | — | — | — | — | — | — | 0.01 |
| D | Purified water | | Remainder | Remainder | Remainder | Remainder | Remainder | Remainder | Remainder |
| | Total | | 100 | 100 | 100 | 100 | 100 | 100 | 100 |
| | pH of sanitizer composition | | 7.0 | 6.9 | 6.9 | 6.9 | 6.9 | 6.9 | 6.6 |
| During rubbing | Resistance and ease of rubbing | Average | 2.2 | 1.5 | 1.6 | 1.8 | 1.6 | 1.3 | 2.2 |
| | | Standard deviation | 0.4 | 0.7 | 0.5 | 0.4 | 0.5 | 0.5 | 0.6 |
| | | Evaluation | A | B | B | B | B | B | A |
| After rubbing | Squeakiness | Average | 2.2 | 1.6 | 1.5 | 1.4 | 0.8 | 0.6 | 2.2 |
| | | Standard deviation | 0.6 | 0.5 | 0.5 | 0.5 | 0.6 | 0.5 | 0.4 |
| | | Evaluation | A | B | B | B | C | C | A |
| | Moisture | Average | 0.5 | 1 | 1.3 | 1.4 | 1.7 | 1.8 | 2.1 |
| | | Standard deviation | 0.5 | 0.5 | 0.7 | 0.5 | 0.5 | 0.4 | 0.3 |
| | | Evaluation | C | B | B | B | B | B | A |

TABLE 2-continued

Table 2 (liquid rub-in hand sanitizer composition)

| | | | | | | | | | |
|---|---|---|---|---|---|---|---|---|---|
| | Slipperiness | Average | 2.7 | 2.5 | 2.3 | 2.1 | 2.1 | 2.0 | 2.2 |
| | | Standard deviation | 0.5 | 0.5 | 0.5 | 0.6 | 0.6 | 0.5 | 0.4 |
| | | Evaluation | A | A | A | A | A | A | A |
| Comprehensive determination | | | Unsuitable | Unsuitable | Unsuitable | Unsuitable | Unsuitable | Unsuitable | Suitable |

mass %

| | | | Test sample | | | | | | |
|---|---|---|---|---|---|---|---|---|---|
| | Component | | 1-8 | 1-9 | 1-10 | 1-11 | 1-12 | 1-13 | 1-14 |
| A | Ethanol* | | 78.1 | 78.1 | 78.1 | 78.1 | 78.1 | 78.1 | 78.1 |
| | Isopropanol | | — | — | — | — | — | — | — |
| | n-Propyl alcohol | | — | — | — | — | — | — | — |
| B | Glycerin | | 0.5 | 0.5 | 0.5 | 0.5 | 0.5 | 0.5 | 0.5 |
| C | Isopropyl myristate | | 0.01 | 0.01 | 0.12 | 0.20 | 0.05 | 0.12 | 0.15 |
| | Glycerin fatty acid ester | | 0.12 | 0.20 | 0.01 | 0.01 | 0.05 | 0.12 | 0.15 |
| D | Purified water | | Remainder | Remainder | Remainder | Remainder | Remainder | Remainder | Remainder |
| | Total | | 100 | 100 | 100 | 100 | 100 | 100 | 100 |
| | pH of sanitizer composition | | 6.5 | 6.5 | 6.6 | 6.6 | 6.7 | 6.6 | 6.5 |
| During rubbing | Resistance and ease of rubbing | Average | 2.4 | 2.5 | 2.2 | 2.3 | 2.6 | 2.5 | 2.5 |
| | | Standard deviation | 0.5 | 0.7 | 0.4 | 0.5 | 0.5 | 0.5 | 0.5 |
| | | Evaluation | A | A | A | A | A | A | A |
| After rubbing | Squeakiness | Average | 2.5 | 2.6 | 2.5 | 2.5 | 2.4 | 2.5 | 2.3 |
| | | Standard deviation | 0.5 | 0.5 | 0.5 | 0.5 | 0.5 | 0.5 | 0.5 |
| | | Evaluation | A | A | A | A | A | A | A |
| | Moisture | Average | 2.3 | 2.5 | 2.4 | 2.3 | 2.4 | 2.4 | 2.4 |
| | | Standard deviation | 0.5 | 0.7 | 0.5 | 0.5 | 0.5 | 0.5 | 0.7 |
| | | Evaluation | A | A | A | A | A | A | A |
| | Slipperiness | Average | 2.4 | 1.4 | 2.1 | 1.8 | 2.2 | 2.1 | 1.5 |
| | | Standard deviation | 0.8 | 0.8 | 0.7 | 0.4 | 0.4 | 0.7 | 0.5 |
| | | Evaluation | A | B | A | B | A | A | B |
| Comprehensive determination | | | Suitable | Unsuitable | Suitable | Unsuitable | Suitable | Suitable | Unsuitable |

*The ethanol concentration of 78.1 mass % corresponds to 83 v/v/%.

TABLE 3

Table 3 (liquid rub-in hand sanitizer composition)

| | | | Test sample | | | | | | | |
|---|---|---|---|---|---|---|---|---|---|---|
| | Component | | 1-15 | 1-16 | 1-17 | 1-18 | 1-19 | 1-20 | 1-21 | 1-22 |
| A | Ethanol* | | 45.8 | 45.8 | 82.5 | 82.5 | — | — | — | — |
| | Isopropanol | | — | — | — | — | 70 | 70 | 80 | 80 |
| | n-Propyl alcohol | | — | — | — | — | — | — | — | — |
| B | Glycerin | | — | 0.5 | — | 0.5 | — | 0.5 | — | 0.5 |
| C | Isopropyl myristate | | — | 0.05 | — | 0.05 | — | 0.05 | — | 0.05 |
| | Glycerin fatty acid ester | | — | 0.05 | — | 0.05 | — | 0.05 | — | 0.05 |
| D | Purified water | | Remainder | Remainder | Remainder | Remainder | Remainder | Remainder | Remainder | Remainder |
| | Total | | 100 | 100 | 100 | 100 | 100 | 100 | 100 | 100 |
| | pH of sanitizer composition | | 6.1 | 6.7 | 6.7 | 6.8 | 6.9 | 6.9 | 6.9 | 6.9 |
| During rubbing | Resistance and ease of rubbing | Average | 2.3 | 2.6 | 2.1 | 2.8 | 2.1 | 2.2 | 2.1 | 2.3 |
| | | Standard deviation | 0.5 | 0.5 | 0.6 | 0.4 | 0.3 | 0.4 | 0.3 | 0.5 |
| | | Evaluation | A | A | A | A | A | A | A | A |
| After rubbing | Squeakiness | Average | 2.3 | 2.6 | 2.2 | 2.4 | 2.2 | 2.2 | 2.2 | 2.3 |
| | | Standard deviation | 0.5 | 0.5 | 0.6 | 0.5 | 0.4 | 0.6 | 0.4 | 0.5 |
| | | Evaluation | A | A | A | A | A | A | A | A |
| | Moisture | Average | 0.6 | 2.5 | 0.2 | 2.1 | 0.4 | 2.2 | 0.3 | 2.1 |
| | | Standard deviation | 0.5 | 0.5 | 0.4 | 0.3 | 0.5 | 0.4 | 0.5 | 0.3 |
| | | Evaluation | C | A | C | A | C | A | C | A |
| | Slipperiness | Average | 2.8 | 2.2 | 2.8 | 2.3 | 2.6 | 2.1 | 2.5 | 2.3 |
| | | Standard deviation | 0.4 | 0.4 | 0.4 | 0.5 | 0.5 | 0.3 | 0.5 | 0.5 |
| | | Evaluation | A | A | A | A | A | A | A | A |

TABLE 3-continued

| Table 3 (liquid rub-in hand sanitizer composition) | | | | | | | | | | |
|---|---|---|---|---|---|---|---|---|---|---|
| | Comprehensive determination | | Unsuitable | Suitable | Unsuitable | Suitable | Unsuitable | Suitable | Unsuitable | Suitable |
| | | | Test sample | | | | | | | |
| | Component | | 1-23 | 1-24 | 1-25 | 1-26 | 1-27 | 1-28 | 1-29 | 1-30 |
| A | Ethanol* | | — | — | — | — | 78.1 | 78.1 | — | — |
| | Isopropanol | | — | — | — | — | 3.4 | 3.4 | 60 | 60 |
| | n-Propyl alcohol | | 70 | 70 | 80 | 80 | — | — | 10 | 10 |
| B | Glycerin | | — | 0.5 | — | 0.5 | — | 0.5 | — | 0.5 |
| C | Isopropyl myristate | | — | 0.05 | — | 0.05 | — | 0.05 | — | 0.05 |
| | Glycerin fatty acid ester | | — | 0.05 | — | 0.05 | — | 0.05 | — | 0.05 |
| D | Purified water | | Remainder | Remainder | Remainder | Remainder | Remainder | Remainder | Remainder | Remainder |
| | Total | | 100 | 100 | 100 | 100 | 100 | 100 | 100 | 100 |
| | pH of sanitizer composition | | 7.4 | 7.4 | 7.4 | 7.4 | 6.9 | 6.7 | 7.0 | 6.6 |
| During rubbing | Resistance and ease of rubbing | Average | 2.1 | 2.2 | 2.2 | 2.2 | 2.3 | 2.6 | 2.1 | 2.3 |
| | | Standard deviation | 0.6 | 0.6 | 0.4 | 0.6 | 0.5 | 0.5 | 0.3 | 0.5 |
| | | Evaluation | A | A | A | A | A | A | A | A |
| After rubbing | Squeakiness | Average | 2.4 | 2.4 | 2.4 | 2.3 | 2.4 | 2.1 | 2.4 | 2.4 |
| | | Standard deviation | 0.7 | 0.7 | 0.7 | 0.5 | 0.5 | 0.7 | 0.7 | 0.5 |
| | | Evaluation | A | A | A | A | A | A | A | A |
| | Moisture | Average | 0.4 | 2.3 | 0.3 | 2.1 | 0.8 | 2.3 | 0.2 | 2.1 |
| | | Standard deviation | 0.5 | 0.5 | 0.5 | 0.6 | 0.6 | 0.5 | 0.4 | 0.6 |
| | | Evaluation | C | A | C | A | C | A | C | A |
| | Slipperiness | Average | 2.6 | 2.3 | 2.7 | 2.4 | 2.6 | 2.2 | 2.5 | 2.1 |
| | | Standard deviation | 0.5 | 0.5 | 0.5 | 0.5 | 0.5 | 0.4 | 0.5 | 0.6 |
| | | Evaluation | A | A | A | A | A | A | A | A |
| | Comprehensive determination | | Unsuitable | Suitable | Unsuitable | Suitable | Unsuitable | Suitable | Unsuitable | Suitable |

*The ethanol concentration of 78.1 mass % corresponds to 83 v/v/%.
Further, the ethanol concentration of 45.8 mass % corresponds to 50 v/v %, and 82.5 mass % corresponds to 90 v/v %.

Although the addition of polyhydric alcohol provided a little more moisture than ethanol alone, it was difficult to rub in because there was a slight feeling of resistance just before drying, and after rubbing in, there was a slight creaky and squeaky feeling (Table 2: test samples 1-2 to 1-6). In addition, the squeaky feeling tended to increase by increasing the mixing amount of polyhydric alcohol (Table 2: test samples 1-5 and 1-6). In contrast, when isopropyl myristate and a glycerin fatty acid ester were combined at a specific ratio, the feeling of resistance during rubbing disappeared, the ease of rubbing was improved, and the squeaky feeling after rubbing was also eliminated. Further, moisture was enhanced, and a moist feeling was obtained (Table 2: test samples 1-7, 1-8, 1-10, 1-12, and 1-13). However, it was confirmed that when the mixing amount of at least one of isopropyl myristate and a glycerin fatty acid ester exceeded 0.12 mass % and reached 0.15 mass % or more, a slippery feeling remained after rubbing, reducing the feel in use (Table 2: test samples 1-9, 1-11, and 1-14).

In addition, as shown in Table 3, the same tendency was also observed when the ethanol concentration was set to 50 vol % or 90 vol %, and when isopropyl alcohol or n-propyl alcohol was used as the lower alcohol (test samples 1-15 to 1-30).

Experimental Example 2: Preparation and Evaluation of Viscous Rub-In Hand Sanitizer Compositions The components shown in Tables 4 to 8 were mixed to prepare viscous rub-in hand sanitizer compositions (test samples 2-1 to 2-47; pH: 6.5 to 7). These compositions were each placed in a dispenser with a single discharge amount set to 1 ml.

Ten panelists evaluated the feel in use when each of the test samples 2-1 to 2-47 was rubbed into the hands and fingers (during rubbing and after rubbing) in the same manner as in Experimental Example 1. Tables 4 to 8 show the test results.

TABLE 4

| Table 4 (viscous rub-in hand sanitizer composition) | | | | | | | | |
|---|---|---|---|---|---|---|---|---|
| | | | | | | | | mass % |
| | | Test sample | | | | | | |
| | Component | 2-1 | 2-2 | 2-3 | 2-4 | 2-5 | 2-6 | 2-7 |
| A | Ethanol* | 78.1 | 78.1 | 78.1 | 78.1 | 78.1 | 78.1 | 78.1 |
| B | Glycerin | 0.01 | 0.5 | 1 | 1.5 | 2 | 0.5 | 0.5 |
| | 1,3-Butylene glycol | — | — | — | — | — | — | — |

TABLE 4-continued

Table 4 (viscous rub-in hand sanitizer composition)

mass %

| | Component | | | 2-1 | 2-2 | 2-3 | 2-4 | 2-5 | 2-6 | 2-7 |
|---|---|---|---|---|---|---|---|---|---|---|
| | | | | Test sample | | | | | | |
| | Propylene glycol | | | — | — | — | — | — | — | — |
| C | Isopropyl myristate | | | — | — | — | — | — | 0.1 | — |
| | Glycerin fatty acid ester | | | — | — | — | — | — | — | 0.1 |
| | Carboxyvinyl polymer | | | 0.15 | 0.15 | 0.15 | 0.15 | 0.15 | 0.15 | 0.15 |
| F | (Acrylates/alkyl acrylate (C10-30)) crosspolymer | | | — | — | — | — | — | — | — |
| E | Triethanolamine | | | 0.23 | 0.23 | 0.23 | 0.23 | 0.23 | 0.23 | 0.23 |
| D | Purified water | | | Remainder | Remainder | Remainder | Remainder | Remainder | Remainder | Remainder |
| | Total | | | 100 | 100 | 100 | 100 | 100 | 100 | 100 |
| | pH of sanitizer composition | | | 6.5 | 6.5 | 6.5 | 6.5 | 6.5 | 6.5 | 6.5 |
| During rubbing | Resistance and ease of rubbing | | Average | 0.8 | 0.7 | 1.1 | 1.2 | 1.3 | 1.4 | 1.4 |
| | | | Standard deviation | 0.8 | 0.7 | 0.7 | 0.6 | 0.5 | 0.5 | 0.5 |
| | | | Evaluation | C | C | B | B | B | B | B |
| After rubbing | Squeakiness | | Average | 1.5 | 1.5 | 1.3 | 1.4 | 1.4 | 1.5 | 1.5 |
| | | | Standard deviation | 0.7 | 0.7 | 0.8 | 0.5 | 0.7 | 0.5 | 0.5 |
| | | | Evaluation | B | B | B | B | B | B | B |
| | Moisture | | Average | 1.0 | 1.2 | 1.5 | 2.0 | 1.9 | 1.8 | 1.8 |
| | | | Standard deviation | 0.5 | 0.4 | 0.8 | 0.7 | 0.6 | 0.4 | 0.4 |
| | | | Evaluation | B | B | B | A | B | B | B |
| | Slipperiness | | Average | 2.4 | 2.2 | 2.1 | 1.8 | 2.0 | 1.8 | 1.7 |
| | | | Standard deviation | 0.5 | 0.6 | 0.3 | 0.6 | 0.5 | 0.4 | 0.5 |
| | | | Evaluation | A | A | A | B | A | B | B |
| | Comprehensive determination | | | Unsuitable | Unsuitable | Unsuitable | Unsuitable | Unsuitable | Unsuitable | Unsuitable |

*The ethanol concentration of 78.1 mass % corresponds to 83 v/v/%.

As shown in Table 4, the viscous sanitizer compositions containing ethanol, a carboxyvinyl polymer as a thickener, and a polyhydric alcohol provided a little more moisture than the viscous sanitizer composition containing ethanol alone (see Table 2: test sample 1-1); however, they were difficult to rub in because there was a feeling of resistance just before drying, and after rubbing in, there was a slight creaky and squeaky feeling (test samples 2-1 to 2-5). When the mixing amount of polyhydric alcohol was as low as 0.5 mass % or less, the feeling of resistance tended to be high during rubbing, making it difficult to rub in (test samples 2-1 to 2-2). Even when one of isopropyl myristate and a glycerin fatty acid ester was added, no improvement was observed in resistance during rubbing (ease of rubbing), squeaky feeling after rubbing, or moisture (test samples 2-6 and 2-7).

TABLE 5

Table 5 (viscous rub-in hand sanitizer composition)

| | Component | | | 2-8 | 2-9 | 2-10 | 2-11 | 2-12 | 2-13 | 2-14 | 2-15 | 2-16 |
|---|---|---|---|---|---|---|---|---|---|---|---|---|
| | | | | Test sample | | | | | | | | |
| A | Ethanol* | | | 78.1 | 78.1 | 78.1 | 78.1 | 78.1 | 78.1 | 78.1 | 78.1 | 78.1 |
| B | Glycerin | | | 0.5 | 0.5 | 0.5 | 0.5 | 0.5 | 0.5 | 0.5 | 0.5 | 0.5 |
| | 1,3-Butylene glycol | | | — | — | — | — | — | — | — | — | — |
| | Propylene glycol | | | — | — | — | — | — | — | — | — | — |
| C | Isopropyl myristate | | | 0.01 | 0.01 | 0.01 | 0.01 | 0.10 | 0.10 | 0.10 | 0.12 | 0.12 |
| | Glycerin fatty acid ester | | | 0.01 | 0.10 | 0.12 | 0.20 | 0.01 | 0.10 | 0.20 | 0.01 | 0.12 |
| F | Carboxyvinyl polymer | | | 0.15 | 0.15 | 0.15 | 0.15 | 0.15 | 0.15 | 0.15 | 0.15 | 0.15 |
| | (Acrylates/alkyl acrylate (C10-30) crosspolymer | | | — | — | — | — | — | — | — | — | — |
| E | Triethanolamine | | | 0.023 | 0.023 | 0.023 | 0.023 | 0.023 | 0.023 | 0.023 | 0.023 | 0.023 |
| D | Purified water | | | Remainder | Remainder | Remainder | Remainder | Remainder | Remainder | Remainder | Remainder | Remainder |
| | Total | | | 100 | 100 | 100 | 100 | 100 | 100 | 100 | 100 | 100 |
| | pH of sanitizer composition | | | 6.6 | 6.6 | 6.5 | 6.5 | 6.5 | 6.7 | 6.6 | 6.6 | 6.6 |
| During rubbing | Resistance and ease of rubbing | | Average | 2.4 | 2.4 | 2.4 | 2.3 | 2.4 | 2.4 | 2.4 | 2.5 | 2.5 |
| | | | Standard deviation | 0.5 | 0.5 | 0.7 | 0.7 | 0.7 | 0.7 | 0.7 | 0.5 | 0.5 |
| | | | Evaluation | A | A | A | A | A | A | A | A | A |
| After rubbing | Squeakiness | | Average | 2.3 | 2.2 | 2.5 | 2.2 | 2.3 | 2.5 | 2.6 | 2.5 | 2.3 |
| | | | Standard deviation | 0.5 | 0.4 | 0.5 | 0.4 | 0.5 | 0.5 | 0.5 | 0.5 | 0.5 |
| | | | Evaluation | A | A | A | A | A | A | A | A | A |

TABLE 5-continued

Table 5 (viscous rub-in hand sanitizer composition)

| Component | | | 2-8 | 2-9 | 2-10 | 2-11 | 2-12 | 2-13 | 2-14 | 2-15 | 2-16 |
|---|---|---|---|---|---|---|---|---|---|---|---|
| | | | Test sample | | | | | | | | |
| | Moisture | Average | 2.1 | 2.3 | 2.3 | 2.4 | 2.3 | 2.3 | 2.6 | 2.3 | 2.2 |
| | | Standard deviation | 0.3 | 0.5 | 0.5 | 0.5 | 0.5 | 0.5 | 0.5 | 0.5 | 0.6 |
| | | Evaluation | A | A | A | A | A | A | A | A | A |
| | Slipperiness | Average | 2.2 | 2.5 | 2.4 | 1.7 | 2.4 | 2.2 | 1.6 | 2.1 | 2.0 |
| | | Standard deviation | 0.4 | 0.5 | 0.8 | 1.2 | 0.8 | 0.8 | 1.1 | 0.7 | 0.5 |
| | | Evaluation | A | A | A | B | A | A | B | A | A |
| Comprehensive determination | | | Suitable | Suitable | Suitable | Unsuitable | Suitable | Suitable | Unsuitable | Suitable | Suitable |

*The ethanol concentration of 78.1 mass % corresponds to 83 v/v/%.

TABLE 6

Table 6 (viscous rub-in hand sanitizer composition)

| | Component | | 2-17 | 2-18 | 2-19 | 2-20 | 2-21 |
|---|---|---|---|---|---|---|---|
| | | | Test sample | | | | |
| A | Ethanol* | | 78.1 | 78.1 | 78.1 | 78.1 | 78.1 |
| B | Glycerin | | 0.5 | 0.5 | 0.5 | 0.5 | 0.5 |
| | 1,3-Butylene glycol | | — | — | — | — | — |
| | Propylene glycol | | — | — | — | — | — |
| C | Isopropyl myristate | | 0.15 | 0.18 | 0.20 | 0.20 | 0.20 |
| | Glycerin fatty acid ester | | 0.15 | 0.18 | 0.01 | 0.10 | 0.20 |
| F | Carboxyvinyl polymer | | 0.15 | 0.15 | 0.15 | 0.15 | 0.15 |
| | (Acrylates/alkyl acrylate (C10-30) crosspolymer | | — | — | — | — | — |
| E | Triethanolamine | | 0.023 | 0.023 | 0.023 | 0.023 | 0.023 |
| D | Purified water | | Remainder | Remainder | Remainder | Remainder | Remainder |
| | Total | | 100 | 100 | 100 | 100 | 100 |
| | pH of sanitizer composition | | 6.5 | 6.6 | 6.6 | 6.6 | 6.7 |
| During rubbing | Resistance and ease of rubbing | Average | 2.3 | 2.2 | 2.3 | 2.2 | 2.1 |
| | | Standard deviation | 0.5 | 0.4 | 0.5 | 0.6 | 0.7 |
| | | Evaluation | A | A | A | A | A |
| After rubbing | Squeakiness | Average | 2.3 | 2.1 | 2.1 | 2.2 | 2.2 |
| | | Standard deviation | 0.5 | 0.6 | 0.3 | 0.4 | 0.6 |
| | | Evaluation | A | A | A | A | A |
| | Moisture | Average | 2.3 | 2.4 | 2.3 | 2.5 | 2.6 |
| | | Standard deviation | 0.5 | 0.5 | 0.5 | 0.7 | 0.5 |
| | | Evaluation | A | A | A | A | A |
| | Slipperiness | Average | 1.7 | 1.8 | 1.7 | 1.5 | 1.1 |
| | | Standard deviation | 0.8 | 0.4 | 0.5 | 0.5 | 0.9 |
| | | Evaluation | B | B | B | B | B |
| | Comprehensive determination | | Unsuitable | Unsuitable | Unsuitable | Unsuitable | Unsuitable |

*The ethanol concentration of 78.1 mass % corresponds to 83 v/v/%.

As shown in Table 5, it was confirmed that when viscous sanitizer compositions containing ethanol, a carboxyvinyl polymer as a thickener, and a polyhydric alcohol were further combined with isopropyl myristate and a glycerin fatty acid ester each at a ratio of 0.01 to 0.12 mass %, the resulting hand sanitizer compositions were easy to rub in with no resistance during rubbing, and had no squeaky or slippery feeling after rubbing, were moist and moisturized, and had a good feel in use (test samples 2-8 to 10, 2-12 and 13, 2-15 and 16). In contrast, as shown in Tables 5 and 6, it was confirmed that when the mixing amount of one of isopropyl myristate and a glycerin fatty acid ester exceeded 0.12 mass % and reached 0.15 mass % or more, a slippery feeling remained after rubbing, reducing the feel in use (test samples 2-11, 2-14, and 2-17 to 21).

TABLE 7

Table 7 (viscous rub-in hand sanitizer composition)

| | Component | 2-22 | 2-23 | 2-24 | 2-25 | 2-26 | 2-27 |
|---|---|---|---|---|---|---|---|
| | | Test sample | | | | | |
| A | Ethanol* | 78.1 | 78.1 | 78.1 | 78.1 | 78.1 | 78.1 |
| | Isopropanol | — | — | — | — | — | — |

TABLE 7-continued

Table 7 (viscous rub-in hand sanitizer composition)

| | | | | | | | | |
|---|---|---|---|---|---|---|---|---|
| | n-Propyl alcohol (also possible with n-propanol) | | — | — | — | — | — | — |
| B | Glycerin | | 0.01 | 0.1 | 0.5 | 1 | 1.5 | 2 |
| | 1,3-Butylene glycol | | — | — | — | — | — | — |
| | Propylene glycol | | — | — | — | — | — | — |
| C | Isopropyl myristate | | 0.05 | 0.05 | 0.05 | 0.05 | 0.05 | 0.05 |
| | Glycerin fatty acid ester | | 0.05 | 0.05 | 0.05 | 0.05 | 0.05 | 0.05 |
| F | Carboxyvinyl polymer | | 0.15 | 0.15 | 0.15 | 0.15 | 0.15 | 0.15 |
| | (Acrylates/alkyl acrylate (C10-30)) crosspolymer | | — | — | — | — | — | — |
| E | Triethanolamine | | 0.023 | 0.023 | 0.023 | 0.023 | 0.023 | 0.023 |
| D | Purified water | | Remainder | Remainder | Remainder | Remainder | Remainder | Remainder |
| | Total | | 100 | 100 | 100 | 100 | 100 | 100 |
| | pH of sanitizer composition | | 6.6 | 6.6 | 6.6 | 6.6 | 6.6 | 6.6 |
| During rubbing | Resistance and ease of rubbing | Average | 2.4 | 2.5 | 2.5 | 2.2 | 1.8 | 1.7 |
| | | Standard deviation | 0.5 | 0.5 | 0.5 | 0.6 | 0.6 | 0.5 |
| | | Evaluation | A | A | A | A | B | B |
| After rubbing | Squeakiness | Average | 2.5 | 2.3 | 2.3 | 2.1 | 1.6 | 1.6 |
| | | Standard deviation | 0.5 | 0.5 | 0.5 | 0.6 | 0.5 | 0.5 |
| | | Evaluation | A | A | A | A | B | B |
| | Moisture | Average | 2.1 | 2.3 | 2.3 | 2.2 | 1.9 | 1.9 |
| | | Standard deviation | 0.7 | 0.7 | 0.8 | 0.4 | 0.6 | 0.6 |
| | | Evaluation | A | A | A | A | B | B |
| | Slipperiness | Average | 2.3 | 2.3 | 2.2 | 2.4 | 2.2 | 1.7 |
| | | Standard deviation | 0.5 | 0.5 | 0.4 | 0.5 | 0.8 | 1.1 |
| | | Evaluation | A | A | A | A | A | B |
| | Comprehensive determination | | Suitable | Suitable | Suitable | Suitable | Unsuitable | Unsuitable |

| | | | Test sample | | | | |
|---|---|---|---|---|---|---|---|
| | Component | | 2-28 | 2-29 | 2-30 | 2-31 | 2-32 |
| A | Ethanol* | | 78.1 | 78.1 | 78.1 | 78.1 | 78.1 |
| | Isopropanol | | — | — | — | — | — |
| | n-Propyl alcohol (also possible with n-propanol) | | — | — | — | — | — |
| B | Glycerin | | — | — | 0.1 | 0.5 | 0.1 |
| | 1,3-Butylene glycol | | 0.5 | — | 0.1 | — | 0.1 |
| | Propylene glycol | | — | 0.5 | 0.1 | — | 0.1 |
| C | Isopropyl myristate | | 0.05 | 0.05 | 0.05 | 0.05 | 0.05 |
| | Glycerin fatty acid ester | | 0.05 | 0.05 | 0.05 | 0.05 | 0.05 |
| F | Carboxyvinyl polymer | | 0.15 | 0.15 | 0.15 | 0.10 | — |
| | (Acrylates/alkyl acrylate (C10-30)) crosspolymer | | — | — | — | 0.05 | 0.15 |
| E | Triethanolamine | | 0.023 | 0.023 | 0.023 | 0.023 | 0.023 |
| D | Purified water | | Remainder | Remainder | Remainder | Remainder | Remainder |
| | Total | | 100 | 100 | 100 | 100 | 100 |
| | pH of sanitizer composition | | 6.6 | 6.6 | 6.6 | 6.6 | 6.6 |
| During rubbing | Resistance and ease of rubbing | Average | 2.7 | 2.5 | 2.4 | 2.4 | 2.3 |
| | | Standard deviation | 0.5 | 0.5 | 0.5 | 0.5 | 0.5 |
| | | Evaluation | A | A | A | A | A |
| After rubbing | Squeakiness | Average | 2.6 | 2.3 | 2.3 | 2.3 | 2.4 |
| | | Standard deviation | 0.5 | 0.7 | 0.7 | 0.5 | 0.5 |
| | | Evaluation | A | A | A | A | A |
| | Moisture | Average | 2.3 | 2.2 | 2.2 | 2.3 | 2.3 |
| | | Standard deviation | 0.5 | 0.6 | 0.6 | 0.5 | 0.5 |
| | | Evaluation | A | A | A | A | A |
| | Slipperiness | Average | 2.3 | 2.4 | 2.5 | 2.3 | 2.4 |
| | | Standard deviation | 0.7 | 0.5 | 0.5 | 0.5 | 0.5 |
| | | Evaluation | A | A | A | A | A |
| | Comprehensive determination | | Suitable | Suitable | Suitable | Suitable | Suitable |

*The ethanol concentration of 78.1 mass % corresponds to 83 v/v/%.

TABLE 8

Table 8 (viscous rub-in hand sanitizer composition)

| | Component | | | 2-33 | 2-34 | 2-35 | 2-36 | 2-37 | 2-38 | 2-39 | 2-40 |
|---|---|---|---|---|---|---|---|---|---|---|---|
| | | | | Test sample | | | | | | | |
| A | Ethanol* | | | 78.1 | 78.1 | 78.1 | 78.1 | 78.1 | 78.1 | 45.8 | 82.5 |
| | Isopropanol | | | — | — | — | — | — | — | — | — |
| | n-Propyl alcohol | | | — | — | — | — | — | — | — | — |
| B | Glycerin | | | 0.5 | 0.5 | 0.5 | 0.5 | 0.5 | 0.5 | 0.5 | 0.5 |
| | 1,3-Butylene glycol | | | — | — | — | — | — | — | — | — |
| | Propylene glycol | | | — | — | — | — | — | — | — | — |
| C | Isopropyl myristate | | | 0.05 | 0.05 | 0.05 | 0.05 | 0.05 | 0.05 | 0.05 | 0.05 |
| | Glycerin fatty acid ester | | | 0.05 | 0.05 | 0.05 | 0.05 | 0.05 | 0.05 | 0.05 | 0.05 |
| F | Carboxyvinyl polymer | | | 0.05 | 0.5 | 1.0 | — | — | — | 0.15 | 0.15 |
| | (Acrylates/alkyl acrylate (C10-30)) crosspolymer | | | — | — | — | 0.05 | 0.5 | 1.0 | — | — |
| E | Triethanolamine | | | 0.008 | 0.077 | 0.15 | 0.008 | 0.077 | 0.15 | 0.023 | 0.023 |
| D | Purified water | | | Remainder | Remainder | Remainder | Remainder | Remainder | Remainder | Remainder | Remainder |
| | Total | | | 100 | 100 | 100 | 100 | 100 | 100 | 100 | 100 |
| | pH of sanitizer composition | | | 6.6 | 6.6 | 6.6 | 6.6 | 6.6 | 6.6 | 6.4 | 6.7 |
| During rubbing | Resistance and ease of rubbing | Average | | 2.7 | 2.1 | 2.0 | 2.7 | 2.0 | 2.0 | 2.4 | 2.5 |
| | | Standard deviation | | 0.5 | 0.7 | 0.8 | 0.5 | 0.5 | 0.8 | 0.5 | 0.5 |
| | | Evaluation | | A | A | A | A | A | A | A | A |
| After rubbing | Squeakiness | Average | | 2.3 | 2.3 | 2.3 | 2.2 | 2.3 | 2.4 | 2.3 | 2.3 |
| | | Standard deviation | | 0.7 | 0.5 | 0.5 | 0.6 | 0.5 | 0.5 | 0.5 | 0.5 |
| | | Evaluation | | A | A | A | A | A | A | A | A |
| | Moisture | Average | | 2.1 | 2.3 | 2.6 | 2.3 | 2.3 | 2.5 | 2.4 | 2.1 |
| | | Standard deviation | | 0.7 | 0.5 | 0.5 | 0.7 | 0.5 | 0.5 | 0.5 | 0.6 |
| | | Evaluation | | A | A | A | A | A | A | A | A |
| | Slipperiness | Average | | 2.8 | 2.1 | 2.0 | 2.4 | 2.1 | 2.1 | 2.4 | 2.5 |
| | | Standard deviation | | 0.4 | 0.3 | 0.9 | 0.5 | 0.7 | 0.7 | 0.5 | 0.5 |
| | | Evaluation | | A | A | A | A | A | A | A | A |
| | Comprehensive determination | | | Suitable | Suitable | Suitable | Suitable | Suitable | Suitable | Suitable | Suitable |

| | Component | | 2-41 | 2-42 | 2-43 | 2-44 | 2-45 | 2-46 | 2-47 |
|---|---|---|---|---|---|---|---|---|---|
| | | | Test sample | | | | | | |
| A | Ethanol* | | 78.1 | — | — | — | — | — | — |
| | Isopropanol | | 3.4 | 70 | 80 | — | — | 60 | 60 |
| | n-Propyl alcohol | | — | — | — | 70 | 80 | 10 | 10 |
| B | Glycerin | | 0.5 | 0.5 | 0.5 | 0.5 | 0.5 | 0.5 | 0.5 |
| | 1,3-Butylene glycol | | — | — | — | — | — | — | — |
| | Propylene glycol | | — | — | — | — | — | — | — |
| C | Isopropyl myristate | | 0.05 | 0.05 | 0.05 | 0.05 | 0.05 | 0.05 | 0.05 |
| | Glycerin fatty acid ester | | 0.05 | 0.05 | 0.05 | 0.05 | 0.05 | 0.05 | 0.05 |
| F | Carboxyvinyl polymer | | 0.15 | 0.15 | 0.15 | 0.15 | 0.15 | 0.15 | — |
| | (Acrylates/alkyl acrylate (C10-30)) crosspolymer | | — | — | — | — | — | — | 0.15 |
| E | Triethanolamine | | 0.023 | 0.023 | 0.023 | 0.023 | 0.023 | 0.023 | 0.023 |
| D | Purified water | | Remainder | Remainder | Remainder | Remainder | Remainder | Remainder | Remainder |
| | Total | | 100 | 100 | 100 | 100 | 100 | 100 | 100 |
| | pH of sanitizer composition | | 6.6 | 6.6 | 6.6 | 6.6 | 6.6 | 6.6 | 6.6 |
| During rubbing | Resistance and ease of rubbing | Average | 2.3 | 2.3 | 2.3 | 2.2 | 2.3 | 2.2 | 2.3 |
| | | Standard deviation | 0.7 | 0.5 | 0.5 | 0.6 | 0.5 | 0.6 | 0.5 |
| | | Evaluation | A | A | A | A | A | A | A |
| After rubbing | Squeakiness | Average | 2.3 | 2.4 | 2.2 | 2.3 | 2.3 | 2.6 | 2.5 |
| | | Standard deviation | 0.8 | 0.5 | 0.4 | 0.7 | 0.7 | 0.5 | 0.5 |
| | | Evaluation | A | A | A | A | A | A | A |
| | Moisture | Average | 2.4 | 2.3 | 2.1 | 2.2 | 2.1 | 2.2 | 2.1 |
| | | Standard deviation | 0.5 | 0.5 | 0.6 | 0.4 | 0.4 | 0.4 | 0.4 |
| | | Evaluation | A | A | A | A | A | A | A |
| | Slipperiness | Average | 2.2 | 2.5 | 2.5 | 2.4 | 2.5 | 2.5 | 2.5 |
| | | Standard deviation | 0.4 | 0.5 | 0.5 | 0.5 | 0.5 | 0.5 | 0.5 |
| | | Evaluation | A | A | A | A | A | A | A |
| | Comprehensive determination | | Suitable | Suitable | Suitable | Suitable | Suitable | Suitable | Suitable |

*The ethanol concentration of 78.1 mass % corresponds to 83 v/v/%.
Further, the ethanol concentration of 45.8 mass % corresponds to 50 v/v %, and 82.5 mass % corresponds to 90 v/v %.

As shown in Table 7, it was confirmed that when viscous sanitizer compositions containing ethanol, a carboxyvinyl polymer, isopropyl myristate, and a glycerin fatty acid ester were mixed with 1.5 mass % or more of polyhydric alcohol, such as glycerin, the feel in use was reduced during rubbing and after rubbing (test samples 2-26 and 27), and that a mixing amount of 0.01 to 1.0 mass % provided a good feel in use (test samples 2-22 to 25). It was also confirmed that when 1,3-butylene glycol or propylene glycol was used in place of glycerin, rub-in hand sanitizer compositions with a good feel in use were similarly obtained (test samples 2-28 to 30), and that when an (acrylates/alkyl acrylate (C10-30)) crosspolymer, which is also an acrylic acid copolymer, was used in place of, or in combination with, the carboxyvinyl polymer, rub-in hand sanitizer compositions with a good feel in use were similarly obtained (Table 7: test samples 2-31 and 32, Table 8: test samples 2-33 to 38).

Further, as shown in Table 8, when the ethanol concentration was set to 50 vol % or 90 vol %, and when isopropyl alcohol or n-propyl alcohol was used as the lower alcohol, a similar good feel in use was observed (test samples 2-39 to 47), as with the sanitizer compositions with an ethanol concentration of 83 vol %.

The invention claimed is:

1. A rub-in hand sanitizer composition having a pH of 5.5 to 7.5 and comprising the following components:

(A) a lower alcohol: 50 to 90 vol %;

(B) at least one polyhydric alcohol selected from the group consisting of glycerin, 1,3-butylene glycol, and propylene glycol: 0.01 to 1.0 mass %;

(C) isopropyl myristate and a glycerin fatty acid ester: each 0.01 to 0.12 mass %; and (D) water, wherein the glycerin fatty acid ester as component (C) is a monoacylglycerol or a diacylglycerol with a fatty acid ester-bonded to one or two of the three hydroxyl groups of glycerin.

2. The rub-in hand sanitizer composition according to claim 1, wherein the lower alcohol is at least one member selected from ethanol, n-propyl alcohol, and isopropyl alcohol.

3. The rub-in hand sanitizer composition according to claim 2, wherein the ratio of isopropyl myristate and glycerin fatty acid ester as component (C) is such that the amount of glycerin fatty acid ester is 8 to 1200 parts by mass based on 100 parts by mass of isopropyl myristate.

4. The rub-in hand sanitizer composition according to claim 3, wherein the glycerin fatty acid ester as component (C) is one in which a $C_{6-16}$ saturated or unsaturated fatty acid is ester-bonded to one hydroxy group of glycerin.

5. The rub-in hand sanitizer composition according to claim 4, further comprising (E) a pH adjuster.

6. The rub-in hand sanitizer composition according to claim 5, which is a liquid hand sanitizer composition.

7. The rub-in hand sanitizer composition according to claim 5, further comprising the following component:

(F) at least one acrylic acid polymer selected from the group consisting of carboxyvinyl polymers and acrylic acid-alkyl methacrylate copolymers.

8. The rub-in hand sanitizer composition according to claim 7, which is a viscous hand sanitizer composition.

9. The rub-in hand sanitizer composition according to claim 7, wherein the carboxyvinyl polymer as component (F) has the following characteristics:

the viscosity of a 0.2 w/v % aqueous solution (pH: 7.0-7.5, 20±1° C.) measured with a Brookfield rotational viscometer (No. 2 or No. 4, 12 rotations) is 1500 to 50000 mPa·s.

10. The rub-in hand sanitizer composition according to claim 7, wherein the acrylic acid-alkyl methacrylate copolymer as component (F) is an (acrylates/alkyl acrylate (C10-30)) crosspolymer having the following characteristics:

the viscosity of a 0.5 w/v % aqueous solution (pH: 7.0-7.5, 20±1° C.) measured with a Brookfield rotational viscometer (No. 2 or No. 4, 12 rotations) is 25000 to 65000 mPa·s.

11. The rub-in hand sanitizer composition according to claim 10, wherein the pH adjuster as component (E) is at least one water-soluble or alcohol-soluble amine compound selected from the group consisting of triethanolamine, aminomethylpropanol, tromethamine, tetrahydroxypropyl ethylenediamine, diisopropanolamine, and PEG-15 Cocamine.

12. The rub-in hand sanitizer composition according to claim 1, wherein the ratio of isopropyl myristate and glycerin fatty acid ester as component (C) is such that the amount of glycerin fatty acid ester is 8 to 1200 parts by mass based on 100 parts by mass of isopropyl myristate.

13. The rub-in hand sanitizer composition according to claim 1, wherein the glycerin fatty acid ester as component (C) is one in which a $C_{6-16}$ saturated or unsaturated fatty acid is ester-bonded to one hydroxy group of glycerin.

14. The rub-in hand sanitizer composition according to claim 1, further comprising (E) a pH adjuster.

15. The rub-in hand sanitizer composition according to claim 1, which is a liquid hand sanitizer composition.

16. The rub-in hand sanitizer composition according to claim 1, further comprising the following component:

(F) at least one acrylic acid polymer selected from the group consisting of carboxyvinyl polymers and acrylic acid-alkyl methacrylate copolymers.

17. The rub-in hand sanitizer composition according to claim 16, wherein the pH adjuster as component (E) is at least one water-soluble or alcohol-soluble amine compound selected from the group consisting of triethanolamine, aminomethylpropanol, tromethamine, tetrahydroxypropyl ethylenediamine, diisopropanolamine, and PEG-15 Cocamine.

18. The rub-in hand sanitizer composition according to claim 16, which is a viscous hand sanitizer composition.

19. The rub-in hand sanitizer composition according to claim 16, wherein the carboxyvinyl polymer as component (F) has the following characteristics:

the viscosity of a 0.2 w/v % aqueous solution (pH: 7.0-7.5, 20±1° C.) measured with a Brookfield rotational viscometer (No. 2 or No. 4, 12 rotations) is 1500 to 50000 mPa·s.

20. The rub-in hand sanitizer composition according to claim 16, wherein the acrylic acid-alkyl methacrylate copolymer as component (F) is an (acrylates/alkyl acrylate (C10-30)) crosspolymer having the following characteristics:

the viscosity of a 0.5 w/v % aqueous solution (pH: 7.0-7.5, 20±1° C.) measured with a Brookfield rotational viscometer (No. 2 or No. 4, 12 rotations) is 25000 to 65000 mPa·s.

* * * * *